(12) United States Patent
Eastman et al.

(10) Patent No.: US 9,987,293 B2
(45) Date of Patent: Jun. 5, 2018

(54) METHOD FOR TREATING CHRONIC LYMPHOCYTIC LEUKEMIA

(71) Applicant: BIONOMICS LIMITED, Thebarton (AU)

(72) Inventors: Alan R. Eastman, Lebanon, NH (US); Darcy Bates, White River Junction, VT (US)

(73) Assignee: BIONOMICS LIMITED, Thebarton (AU)

( * ) Notice: Subject to any disclaimer, the term of this patent is extended or adjusted under 35 U.S.C. 154(b) by 0 days. days.

(21) Appl. No.: 15/301,522

(22) PCT Filed: Apr. 4, 2014

(86) PCT No.: PCT/AU2014/000360
§ 371 (c)(1),
(2) Date: Oct. 3, 2016

(87) PCT Pub. No.: WO2015/149105
PCT Pub. Date: Oct. 8, 2015

(65) Prior Publication Data
US 2017/0112862 A1    Apr. 27, 2017

(51) Int. Cl.
*A61K 31/665*    (2006.01)
*A61K 31/343*    (2006.01)

(52) U.S. Cl.
CPC .......... *A61K 31/665* (2013.01); *A61K 31/343* (2013.01)

(58) Field of Classification Search
None
See application file for complete search history.

(56) References Cited

U.S. PATENT DOCUMENTS

| | | | |
|---|---|---|---|
| 8,198,466 B2 * | 6/2012 | Chaplin ............... | C07D 209/12 549/467 |
| 9,006,284 B2 * | 4/2015 | Kremmidiotis ........ | A61K 31/09 514/469 |
| 2011/0130367 A1 | 6/2011 | Kremmidiotis et al. | |

OTHER PUBLICATIONS

Pettit, G. et al J Nat Prod 2005 vol. 68 pp. 1450-1458.*

* cited by examiner

*Primary Examiner* — Heidi Reese
(74) *Attorney, Agent, or Firm* — McCarter & English, LLP; Maria Laccotripe Zacharakis

(57) ABSTRACT

The present disclosure provides methods for treating chronic lymphocytic leukemia (CLL) with medicaments useful for same. The medicaments can be pharmaceutical compositions or kits comprising compounds of formula (I) or a salt, solvate or prodrug thereof. Specific compounds of the invention include 2-methyl-7-hydroxy-3-(3,4,5-trimethoxybenzoyl)-6-methoxybenzofuran which is also known as BNC105 and disodium 6-methoxy-2-methyl-3-(3,4,5-trimethoxybenzoyl)benzofuran-7-yl phosphate which is also known as BNC 105P.

8 Claims, 13 Drawing Sheets

METHOD FOR TREATING CHRONIC LYMPHOCYTIC LEUKEMIA

RELATED APPLICATIONS

This application is a 35 U.S.C. § 371 national stage filing of International Application No. PCT/AU2014/000360, filed on Apr. 4, 2014, the entire contents of which are incorporated herein by reference.

FIELD

The present disclosure teaches a method of treating chronic lymphocytic leukemia (CLL) with medicaments useful for same.

BACKGROUND

Cancer is typically treated with either chemotherapy and/or radiation therapy. While this type of ablation therapy is often effective to destroy a significant amount of tumor cells, such therapies often leave behind a number of tumor cells that are resistant to the treatment. These resistant cells can proliferate and/or metastasize to form new tumors that are also recalcitrant to treatment. Furthermore, the use of known combinations of chemotherapeutic drugs has given rise to multidrug resistant ('MDR') tumor cells.

The American Cancer Society estimates there will be more" than 15,000 new cases and more than 4,500 deaths from chronic lymphocytic leukemia (CLL) in 2013 alone. This condition is characterized by the accumulation of mature CD5+CD19+CD23+ B lymphocytes in peripheral blood, hone marrow, lymph nodes and spleen, which is thought to be caused by a defect in the pathway to regulated cell death rather than an uncontrolled mechanism of cell proliferation. Such defect can lead to chemoresistance and thus strategies aimed to correct it can serve as additional therapies to traditional chemotherapy or lead to more potent therapeutics. The B-cell lymphoma/leukemia 2 (BCL-2) protein is over-expressed in CLL and therefore represents a target in attempts to overcome the resistance of tumors to anti-cancer treatments. CLL is a debilitating leukemia and hence there is an urgent need for selective treatments for this disease.

Microtubules are filamentous polymers that are key components of the lymphocytic cell cytoskeleton. They are dynamic structures fluctuating between states of polymerisation and depolymerization. This property enables microtubules to modulate cell shape, adhesion, migration and proliferation. Compounds that act as tubulin polymerisation inhibitors (TPI's) directly disrupt microtubule polymerisation processes and consequently have the ability to effect cell shape changes and inhibit cell proliferation. These properties are central to the use of TPI's as therapeutics for the treatment of cancer and in the combinations of the present invention.

TPI compounds are important in the treatment of cancers primarily as a result of their capacity to selectively shut down blood flow through a tumor. Targeting tubulin polymerization inhibition has been a very well validated anti-cancer approach through the development and now extensive clinical use of chemotherapeutic TPI's agents.

TPI's can be classified based on their specific tubulin binding site.

Binding of vinca alkaloids to tubulin defines a site that mediates the tubulin destabilization activity seen with these compounds. The 'vinca' site has been shown to directly bind a number of compounds that effect destabilization of tubulin.

Colchicine binding to tubulin defines an independent binding site that like in the case of the 'vinca' site causes destabilization of tubulin. Although TPI's binding to the 'vinca' sites has been exploited in their use as anti-cancer chemotherapeutics, 'colchicine' site binders have been in comparison neglected, possibly due to the lack of therapeutic margins offered by colchicine. However, more recently a number of 'colchicine' site binding agents have been described that have the ability to cause disruption of blood vessels within solid tumors. These TPI's are referred to as Vascular Disruption Agents (VDA). Many of the 'colchicine' site binding agents that exhibit VDA capability are based on natural products such as combretastatins (CA4P, OXi-4503, AVE-8062), colchicines (ZD6126) and phenylahistin (NPI-2358) while others are synthetic compounds (MN-029 and EPC2407).

TPIs act as VDAs because they interfere with microtubule integrity, leading to cytoskeletal changes of the endothelial cells that line the blood vessels of the tumor. As a result, these usually flat cells become more rounded, and lose their cell to cell contact. These events lead to narrowing of tumor blood vessels and ultimately occlusion of blood flow through the vessels. The tumor selectivity associated with these agents results from the fact that tumor vasculature is weaker and more prone to collapse than normal vasculature. Nonetheless, a number of the dose limiting toxicities associated with VDAs are due to a reduction in blood flow in healthy tissues.

There is a need for a more efficacious and selective treatment of CLL.

SUMMARY

The present disclosure enables an effective treatment for CLL predicated in part on the use of a compound of formula (I) or a salt, solvate or prodrug thereof in the selective and preferential induction of apoptosis of CLL cells. The compound of formula (I) is represented below:

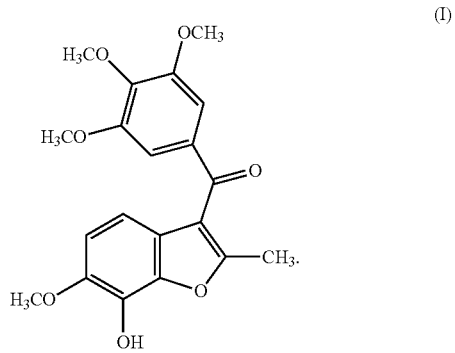 [SMILES: COc1cc(C(=O)c2c(C)oc3c(O)c(OC)ccc23)cc(OC)c1OC]

The compound of formula (I) [2-Methyl-7-hydroxy-3-(3,4,5-trimethoxybenzoyl)-6-methoxybenzofuran] can be prepared by the synthetic methodology described in PCT/AU2007/000101 (WO 07/087684), the contents of which are incorporated by reference.

It is proposed herein that the compound of formula (I) induces selected and preferential apoptosis of CLL cells via the JNK apoptotic pathway in combination with activating NOXA. It is for the proposed reason that only some microtubule drugs are effective in the treatment of certain leukemias. In accordance with the instant disclosure the compounds of formula (I) are found effective against CLL cells facilitating their apoptosis.

Accordingly enabled herein is a method for treating chronic lymphocytic leukemia (CLL) in a patient including the step of administering an effective amount of a compound of formula (I) or a salt, solvate or prodrug thereof

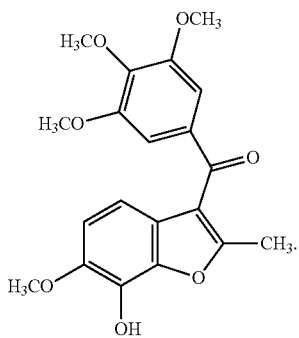
(I)

Further taught herein is the use of a compound of formula (I) or a salt, solvate or prodrug thereof

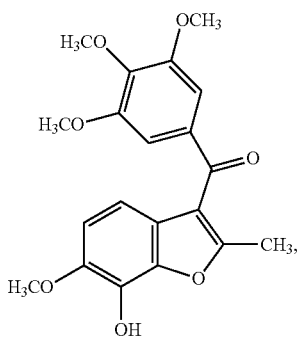
(I)

in the manufacture of a medicament for treating a patient with chronic lymphocytic leukemia (CU.).

In a related embodiment, the present specification is instructive on a compound of formula (I) or a salt, solvate or prodrug thereof

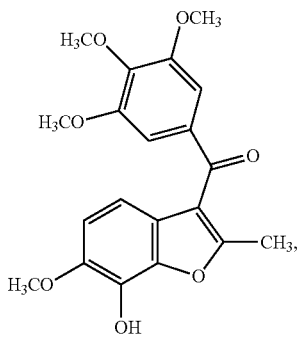
(I)

for use in treating CLL in a patient.

Without wanting to be bound to any particular theory incubation with compounds of formula (I) activates the JNK apoptotic pathway and upregulates functional Noxa in CLL cells at concentrations that cause cleavage of PARP and chromatin condensation. The present compound's activity results in acute apoptosis of CLL cells and thus elucidates a novel and faster mechanism of cell death than previously anticipated for microtubule disrupting agents. The effect of the compound of formula (I) is achieved with an unexpectedly lower concentration than with other microtubule targetous drugs. When incubated with CLL cells, vinblastine and combretastatin A4 show similar effects, but the compounds of formula (I) are a more potent inducer of CU, activated pJNK and Noxa enabling greater levels of selective apoptosis of CLL cells. Furthermore, only a 1-h incubation is sufficient to activate JNK, and apoptosis is still observed 5 h after removal of a compound of formula (I).

The instant specification teaches that apoptosis is dependent on the activation of JNK. Without limiting the present invention to any one theory or mechanism it is proposed herein that both Noxa and JNK are required for this acute apoptosis to occur in CLL cells. JNK was also activated in normal lymphocytes but in the absence of Noxa, were resistant to the compound of formula (I).

Accordingly, in another embodiment the method involves treating a subject in need thereof with an effective amount of the compound of formula (I) in order to induce JNK-dependant apoptosis in CLL cells.

CLL cells are much more resistant to drugs when incubated with stroma cells that mimic the lymph node environment. Therefore, rational drug combinations were tested in an effort to circumvent this resistance. The compound of the present invention is able to induce apoptosis as a single agent through a mechanism that primarily involves BCL-2 and MCL-1 inhibition (see FIG. 10). CLL cells grown on stroma are resistant to ABT-199 (a BCL-2 inhibitor), but are sensitized by compounds of the present invention. This sensitization is likely due to induction of Noxa. However, it is determined herein that the incubation with stroma cells also upregulates BCL-X which elicits resistance to Noxa induction. Since Noxa can also bind to BCL-X when present in excess over the binding capacity of MCL-1, this may also allow for novel drug combinations to overcome the stroma-mediated chemoresistance of CLL cells.

Higher potency is a desired characteristic of a new drug because obviously a lower amount of drug is needed to assert an effect, but it can be detrimental if it is accompanied by higher toxicity or off target effects. The compounds of the present invention do not have any toxic effects as a single agent in peripheral normal lymphocytes even when used at high concentration, comparable to those achievable in plasma. Activation of JNK but no PARP cleavage or Noxa induction is observed. The combination with ABT-199 also results in no overall decrease in survival of normal lymphocytes. Hence, enabled herein is that the compounds of formula (I) is productive in developing new treatment protocols for CLL.

Reference to "CLL" includes its subtypes and its related forms.

BRIEF DESCRIPTION OF THE FIGURES

FIG. 1A depicts Western blots of CLL cells from patient incubated for 6h with 0-1 µM compounds of formula (I);

FIG. 1B depics a survival curve of the same CLL cells measured by chromatin condensation with Hoechst stain.

FIG. 2A depics Western blots of CLL cells from patient 49 incubated for 6h with 0-1 μM compounds of formula (I), vinblastine or combretastatin A4. "C "=a control cell line incubated with 2 μM vinblastine as a positive control for protein expression;

FIG. 2B depicts the survival curve of the same CLL cells measured by chromatin condensation with Hoechst stain.

FIG. 2C depicts a comparison of the survival curves of CLL cells from 3-6 patients incubated for 6h with a compound of formula (I), vinblastine or combretastatin A4 (Mean +/– SEM).

FIG. 3A depicts Western blots of CLL cells from patient 81 which were incubated for 6h with compounds of formula (I), vinblastine or combretastatin A4. "C" +a control cell line incubated with 2 μM vinblastine as a postitive control for protein expression;

FIG. 3B depicts survival curves of the same CLL cells measured by chromatin condensation.

FIG. 4A depicts Western blots of CLL cells from patient 15 incubated for 6h with 0-1 μM compounds of formula (I) (10-1000nM). "C "=a control cell line incubated with 2 μM vinblastine as a positive control for protein expression;

FIG. 4B depicts parallel incubations but performed in the presence of JNK inhibitor VIII.

FIG. 4C depicts the survival curve of the same CLL cells measured by chromatin condensation.

FIG. 5A, left panel, depicts Western blots of CLL cells from patient 66 incubated for 6h with 0-1 μM compounds of formula (I) (1-1000nM);

FIG. 5A, right panel, depicts the same cells incubated with compounds of formula (I) for 1h, then in the absence of media for an additional 5h. "C"=a control cell line incubated with 2 μM vinblastine as a positive control for protein expression.

FIG. 5B depicts the survival curve of the same CLL cells measured by chromatin condensation assay with Hoechst stain.

FIG. 8A depicts survival curves of the CLL cells from patient 66 incubated with compounds of formula (I) alone, or in combination with ABT-199;

FIG. 8C is similar to A except performed on cells from patient 125.

FIG. 9A depicts Western blots of cells from a healthy volunteer incubated for 6h with 0-1 μM compounds of formula (I) alone or with 1-10 nm ABT-199, or 100 nM dinaciclib. "C"=a control cell line incubated with 2 μM vinblastine as a positive control for protein expression;

FIG. 9B depicts the survival curve of the same cells measured by the chromatin condensation assay with Hoechst stain.

FIG. 11A depicts freshly isolated CLL cells incubated for 6h ex vivo with various concentrations of EX2 (n=15);

FIG. 11B depicts cells incubated with EX2 alone or in the presence of JNK Inhibitor VIII.

FIG. 12A depicts the expression of PARP, pJNK, Noxa and Actin proteins (representative sample shown).

FIG. 12B depicts reduced survival due to cellular apoptosis (n=4).

FIG. 13A depicts leukemia cell lines incubated with EX2 ± dinaciclib for 6h;

FIG. 13B depicts CLL cells incubated with EX2 ± ABT-199 (B) for 6h. Consistent with previous vinblastine results, dinaciclib-mediated apoptosis requires JNK but ABT-199-mediated apoptosis does not;

FIG. 13C depicts freshly isolated CLL cells incubated alone and treated immediately, or plated on top of a monolayer of CD40L expressing L4.5 stroma cells for 24h, then treated for 6h with EX2 ± ABT-199 (n=16).

DETAILED DESCRIPTION

Figure 1A:
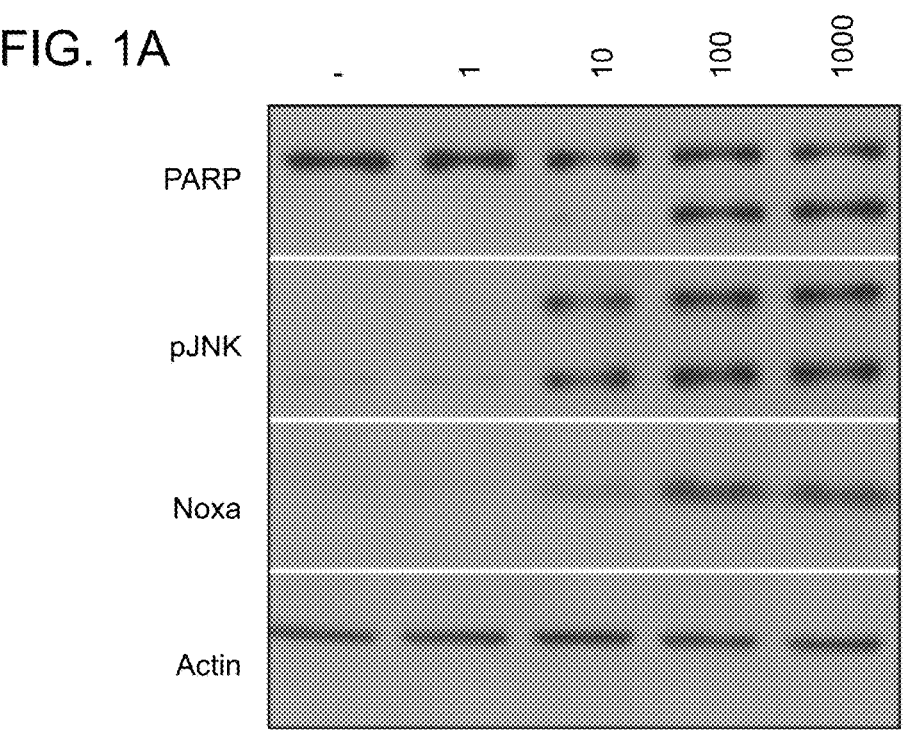
FIG. 1A and 1B depict compounds of formula (I) that induce apoptosis in peripheral CLL cells.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

As used in the subject specification, the singular forms "a", "an" and "the" include the plural aspects unless the context clearly dictates otherwise. Thus, for example, reference to "a CLL cell" includes a single cell, as well as two or more cells; reference to "an agent" includes a single agent, as well as two or more agents; reference to "the disclosure" includes a single and multiple aspects taught by the disclosure; and so forth. Aspects taught and enabled herein are encompassed by the term "invention". All such aspects are enabled within the width of the present invention.

The present disclosure teaches that the compounds of formula (I) are potent tubulin polymerisation inhibitors (TPIs). An important aspect of the compounds of formula (I) is the combination of the specific C-6 and C-7 substituents together with the C-2 Q-group (especially C-2 methyl) which appears to confer greater potency and selectivity when compared to other structurally related TPI compounds. In these compounds, selectivity is not reliant on the predisposition of tumor vasculature towards collapse when challenged with the VDA but on a capacity of the VDA to distinguish between tumor endothelial cells and normal endothelial cells. Normal endothelial cells, found in healthy tissues, are in a "quiescent" state and tumor endothelial cells are in an "activated" state. Most VDAs do not distinguish between these two states, for example, Combretastatin A4 (CA4) is equally potent against quiescent and activated endothelial cells. However, the compounds of formula (I) show selectivity towards tumor endothelial cells (activated) over normal endothelial cells (quiescent).

It will be appreciated that the compound of formula (I) can be administered to a subject as a pharmaceutically acceptable salt thereof. Suitable pharmaceutically acceptable salts include, but are not limited to salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, editic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium. In an embodiment, the method described herein includes within its scope cationic salts e.g. sodium or potassium salts, or alkyl esters (e.g. methyl, ethyl) of the phosphate group.

It will also be appreciated that any compound that is a prodrug of a compound of formula (I) is also within the scope and spirit of the therapeutic protocol herein described. The term "pro-drug" is used in its broadest sense and encompasses those derivatives that are converted in vivo to a compound of the invention (for instance, a compound of formula (I). Such derivatives would readily occur to those skilled in the art, and include, for example, compounds where the free hydroxy group (for instance at C-7 position or $R^{1D}$) is converted into an ester, such as an acetate or phosphate ester, or where a free amino group (for instance at C-7 position or $R^{1D}$) is converted into an amide (e.g., α-aminoacid amide). Procedures for esterifying, e.g. acylating, the compounds are well known in the art and may include treatment of the compound with an appropriate carboxylic acid, anhydride or chloride in the presence of a suitable catalyst or base. One prodrug is a disodium phosphate ester. The disodium phosphate ester (e.g., a C-7 disodium phosphate ester of a compound of formula I) of the compound of the present invention may be useful in increasing the solubility of the compounds. This would, for instance, may allow for delivery of the compound in a benign vehicle like saline. The disodium phosphate ester may be prepared in accordance with the methodology described in Pettit, G. R., et al, *Anticancer Drug Des.*, 1995, 10, 299. Other texts which generally describe prodrugs (and the preparation thereof) include: *Design of Prodrugs*, 1985, H. Bundgaard (Elsevier); *The Practice of Medicinal Chemistry*, 1996, Camille G. Wermuth et al., Chapter 31 (Academic Press); and *A Textbook of Drug Design and Development*, 1991, Bundgaard et. al., Chapter 5, (Harwood Academic Publishers).

Accordingly in an embodiment the compound of formula (I) is a compound represented as:

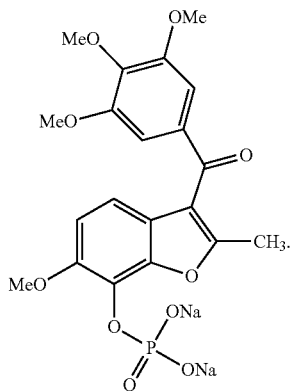

The compounds of formula (I) (or a salt or prodrug thereof) may be in crystalline form either as the free compound or as a solvate (e.g. hydrate) and it is intended that both forms are within the scope of the present invention. Methods of solvation are generally known within the art.

An "effective amount" is intended to mean that the amount of formula (I), or a salt or prodrug thereof when administered to a subject in need of such treatment, is sufficient to effect treatment for CLL. Thus, for example, a therapeutically effective amount is a quantity sufficient to reduce or alleviate CLL. Reference to a subject includes a human of any age. By being in need of such treatment includes patients suspected of having a high genetic or familial risk of developing CLL in an imminent time frame.

Treatment includes at least partially attaining the desired effect, or delaying the onset of or inhibiting the progression of, or halting or reversing altogether the onset or progression of CLL.

In an embodiment, treatment is assessed by an amelioration of symptoms of CLL.

Clinical studies such as open-label, dose escalation studies in patients with CLL proliferative diseases are contemplated herein to identify synergism of a compound of formula (I) and another anti-cancer agent. The beneficial and/or synergistic effects can be determined directly through the results of these studies which are known as such to a person skilled in the art. These studies are also able to compare the effects of a monotherapy using a compound of formula (I), the active ingredients alone or in combination with another agent. In an embodiment, the dose of combination partner (a) may be escalated until the Maximum Tolerated Dosage (MTD) is reached, and agent (b) is administered as a fixed dose. Alternatively, combination partner (a) is administered in a fixed dose and the dose of agent (b) is escalated. Each patient may receive doses of agent (a) either daily or intermittent. The efficacy of the treatment can be determined in such studies, e.g., after 6, 12, 18 or 24 weeks by evaluation of symptom scores every 9 weeks. In this embodiment one of partner (a) or agent (b) is considered a compound of formula (I).

Other combination partners include other anti-cancer compounds, for instance, partners from the group consisting of Alemtuzumab, Ambochlorin (Chlorambucil), Amboclorin (Chlorambucil), Arzerra (Ofatumumab), Bendamustine Hydrochloride, Campath (Alemtuzumab), Chlorambucil, Clafen (Cyclophosphamide), Cyclophosphamide, Cytoxan (Cyclophosphamide), Fludara (Fludarabine Phosphate), Fludarabine Phosphate, Gazyva (Obinutuzumab), Ibrutinib, Imbruvica (Ibrutinib), Leukeran (Chlorambucil), Linfolizin (Chlorambucil), Neosar (Cyclophosphamide), Obinutuzumab, Ofatumumab, and Treanda (Bendamustine Hydrochloride).

The administration of the pharmaceutical combination of the present invention may result not only in a beneficial effect, e.g., an additive or synergistic therapeutic effect, for instance, with regard to alleviating, delaying progression of or inhibiting or ameliorating the symptoms of CLL, but also in further surprising beneficial effects. Such other effects may include fewer adverse side effects, an improved quality of life or a decreased morbidity, compared with a monotherapy applying only one of the pharmaceutically active ingredients used in the combination of the present invention.

A further benefit of the instant therapeutic protocol is that lower doses of the active ingredients of the compound of formula (I) can be used. The dosages need not only be smaller but may also be applied less frequently, which may diminish the incidence or severity of side effects.

The treatment protocol herein described may further involve selecting a patient for treatment based on certain clinical parameters such as age, level of progression of the disease and/or other factors. In addition, patients are generally monitored for progression of CLL after initiation of treatment. Hence, after cessation of treatment, additional treatment may be required subsequently dependant on state or level of remission.

The term "administration" relates to the administration of a compound of formula (I), or salt or prodrug thereof, to a single patient. In a combination therapy if its intended to include treatment regimens in which the agents are not necessarily administered by the same route of administration or at the same time. Accordingly, combination partners may be administered together, one after the other or separately in one combined unit dosage form or in two separate unit dosage forms. The unit dosage form may also be a fixed combination such as a pharmaceutical composition which comprises both partners.

In an embodiment, a therapeutically effective amount of a compound of formula (I) may be administered alone or simultaneously or sequentially with another agent and in any order, and the components may be administered separately or as a fixed combination. For example, the method of treating CLL according to the invention may comprise: (i) administration of a first combination partner in free or pharmaceutically acceptable salt form or prodrug form; and (ii) administration of a second combination partner in free or pharmaceutically acceptable salt form or prodrug form, simultaneously or sequentially in any order, in jointly therapeutically effective amounts, preferably in synergistically effective amounts, e.g., in daily or intermittent dosages corresponding to the amounts described herein. The individual combination partners of the combination of the invention may be administered separately at different times during the course of therapy or concurrently in divided or single combination forms. The term administering also encompasses the use of a pro-drug of a combination partner that converts in vivo to the combination partner as such. The present invention is therefore to be understood as embracing all such regimens of simultaneous or alternating treatment and the term "administering" is to be interpreted accordingly.

As such it will be appreciated that a combination of partners may be presented as a "kit of parts" for use in the treatment of CLL. The kit may comprise a package where the combination partners are supplied separately for co-administration with instructions for use in the particular therapy.

The effective dosage may vary depending on the particular compound or pharmaceutical composition employed, the mode of administration, the condition being treated, the severity of the condition being treated. Thus, the dosage regimen is selected in accordance with a variety of factors including the route of administration and the renal and hepatic function of the patient. A physician of ordinary skill can readily determine and prescribe the effective amount of the single active required to alleviate, counter or arrest the progress of the condition.

Daily dosages will, of course, vary depending on a variety of factors, e.g., the compound chosen, the particular condition to be treated and the desired effect. In general, however, satisfactory results are achieved on administration of a compound of formula (I) at daily dosage rates of about 0.05 to 20 mg/kg per day, particularly 1 to 20 mg/kg/per day, e.g. 0.4 to 16 mg/kg per day, as a single dose or in divided doses. The compound may be administered by any conventional route, in particular amorally, e.g., orally, e.g., in the form of tablets, capsules, drink solutions or parenterally, e.g., in the form of injectable solutions or suspensions. Suitable unit dosage forms for oral administration comprise from about 0.02 to 50 mg active ingredient, usually 0.1 to 30 mg and 2 to 25 mg, 4 to 20 mg, together with one or more pharmaceutically acceptable diluents or carriers therefore.

The compound of formula (I) may be administered to a human in a daily dosage range of 0.5 to 1000 mg. Suitable unit dosage forms for oral administration comprise from about 0.1 to 500 mg active ingredient, preferably 5-50 mg/day, more preferably 5-20 mg/day, and most preferably about 7-12 mg/day, together with one or more pharmaceutically acceptable diluents or carriers therefore.

For instance, an administration regime may include adding a compound of formula (I) at an assigned dose level by I.V. on days 1 and 8 (of a 21 day cycle or 28 day cycle). In this embodiment the compound of formula (I) may be dosed at a level of between 4 to 16 mg/m$^2$.

A further benefit is that lower doses of the active ingredient can be used, e.g., that the dosages need not only often be smaller but are also applied less frequently, or can be used in order to diminish the incidence of side effects. This is in accordance with the desires and requirements of the patients to be treated.

The invention also relates to pharmaceutical compositions which comprise compositions of formula (I) or salts or prodrugs thereof, which for instance, contain, e.g., from about 0.1% to about 99.9%, including from about 1% to about 60%, of the active ingredient(s).

The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal patches may also be used to administer the compounds of the invention.

Compositions for rectal administration may be presented as a suppository with a suitable base comprising, for example, cocoa butter, glycerin, gelatine or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use Extemporaneous injection solutions and suspensions may be prepared from sterile powders, granules and tablets of the kind previously described.

In an embodiment unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLES

Synthetic Protocols

Preparation of 2-Bromo-7-acetoxy-3-(3,4,5-trimethoxybenzoyl)-6-methoxybenzofuran

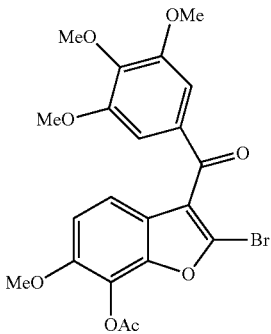 [SMILES: COc1cc(C(=O)c2c(Br)oc3c(OC(C)=O)c(OC)ccc23)cc(OC)c1OC]

Step 1: 2-t-Butyldimethylsilyl-3-(t-butyldimethylsilyloxymethylene)-6-methoxy-7-isopropoxybenzofuran (Larock Coupling)

A suspension of 2-isopropoxy-3-methoxy-5-iodophenol (4.41 mmol), 1-(tert-butyldimethylsilyl)-3-(tert-butyldimethylsilyloxy)propyne (1.5 g, 5.28 mmol), lithium chloride (189 mg, 4.45 mmol) and sodium carbonate (2.34 g, 22.08 mmol) in dry dimethylformamide (5 mL) at 100° C. was deoxygenated 4 times by evacuation and backfilling with nitrogen. Palladium acetate (135 mg, 0.60 mmol) was added and the reaction vessel was degassed twice with nitrogen. The reaction mixture was then stirred at this temperature for 4 hours (tlc) and the solvent was removed by distillation under vacuum. The residue was dissolved in ethyl acetate (75 mL), stirred well, filtered and treated with triethylamine (5 mL). The solution was concentrated onto silica gel (10 g) and purified by flash chromatography (silica gel, eluent=hexane/diethyl ether/triethylamine; 95:5:1%) to afforded the title compound as a yellow oil (1.45 g, 96%); $^1$H NMR (300 MHz, CDCl$_3$) δ 7.24 (d, 1H, J=8.45 Hz), 6.88 (d, 1H, J=8.47 Hz), 4.80 (s, 2H, CH$_2$), 4.73 (m, 1H), 3.88 (s, 3H, OMe), 1.36 (d, 6H, 6.17 Hz), 0.94 (s, 9H), 0.92 (s, 9H), 0.35 (s, 6H), 0.12 (s, 6H).

Step 2: 2-t-Butyldimethylsilyl-3-formyl-6-methoxy-7-isopropoxybenzofuran

To a solution of 2-t-butyldimethylsilyl-3-(t-butyldimethylsilyloxymethylene)-6-methoxy-7-isopropoxybenzofuran (2.69 mmol) in methanol (100 mL) was added concentrated hydrochloric acid (200 μL) and the reaction was stirred for 30 minutes (monitored by tlc), quenched with triethylamine (2 mL) and the solvent removed by distillation under vacuum. The residue was dissolved in dichloromethane (20 mL), washed with water (10 mL), dried over magnesium sulfate, concentrated under vacuum and co-distilled with toluene (20 mL). The crude product was dissolved in dry dichloromethane (4 mL) and added to a stirred solution of Collin's reagent (chromium trioxide (1.01 g), pyridine (1.65 mL) in dry dichloromethane (30 mL)). The suspension was stirred for 10 minutes, filtered and the residue washed with diethyl ether (20 mL). The filtrate was concentrated onto silica (10 g) and purified by flash chromatography (silica gel, eluent=hexane/diethyl-ether/triethylamine (90:9:1) to afford the title compound as a light yellow oil (503 mg, 48%); $^1$H NMR (300 MHz, CDCl$_3$) δ 10.25 (s, 1H, CHO), 7.79 (d, 1H, J=8.45 Hz), 6.98 (d, 1H, J=8.46 Hz), 4.65 (m, 1H), 3.89 (s, 3H, OMe), 1.35 (d, 6H, =6.17 Hz), 0.97 (s, 9H), 0.45 (s, 6H).

Step 3: 2-t-Butyldimethylsilyl-3-(3,4,5-trimethoxybenzoyl)-6-methoxy-7-isopropoxybenzofuran To a stirred solution of 3,4,5-trimethoxyiodobenzene (377 mg, 1.27 mmol) in dry tetrahydrofuran (1 mL) at −78° C. under nitrogen was added n-butyllithium (795 μL, 1.59 mmol, 2M solution in cyclohexane) and the reaction mixture was stirred at this temperature for 40 minutes. After this time a solution of 2-t-butyldimethylsilyl-3-formyl-6-methoxy-7-isoproxybenzofuran (1.07 mmol) in dry tetrahydrofuran (1 mL) was added to the reaction dropwise via syringe pipette. The reaction mixture was stirred at −60° C. for 20 minutes and then allowed to warm to 0° C., stirred for 10 minutes, quenched with saturated ammonium chloride solution (2 mL) and diluted with ethyl acetate (20 mL). The organic layer was washed with water (10 mL), dried over magnesium sulfate and the solvent was removed under vacuum to give a residue that was co-distilled with toluene. The crude product (908 mg) was dissolved in dry tetrahydrofuran (10 mL) and treated with 2,3-dichloro-5,6-dicyano-1,4-benzoquinone (900 mg, 1.59 mmol) was added. The reaction mixture was stirred at room temperature for 16 hours (monitored by tlc) and then loaded onto silica (10 g) and purified by flash chromatography (silica gel, eluent=hexane/diethyl ether/triethylamine, 90:9:1) to afford the title compound as a light yellow oil (498 mg, 69%); $^1$H NMR (300 MHz, CDCl$_3$) δ 7.14 (s, 2H, benzoyl Hs), 6.81 (d, 1H, J=8.64 Hz), 6.77 (d, 1H, J=8.64 Hz) 4.74 (m, 1H), 3.93 (s, 3H, OMe), 3.86 (s, 3H, OMe), 3.78 (s, 6H, 2×OMe), 1.39 (d, 6H, J=6.14 Hz), 1.01 (s, 9H), 0.26 (s, 6H).

Step 4: 2-(tert-butyldimethylsilyloxy)-7-acetoxy-3-(3,4,5-trimethoxybenzoyl)-6-methoxybenzofuran To a stirred solution of 2-(r-butyldimethylsilyloxy)-7-isopropoxy-3-(3,4,5-trimethoxybenzoyl)-6-methoxy-benzofuran (160 mg, 0.31 mmol) in dry DCM (2 mL) at morn temperature under nitrogen was added solid aluminium trichloride (83 mg, 0.62 mmol) and the reaction mixture was stirred for 15 minutes (monitored by tlc). The reaction was quenched with a saturated solution of ammonium chloride, extracted with dichloromethane and dried over magnesium sulfate. The solvent was removed by distillation and residue was dried by azeotropic removal of water with toluene. The crude product was dissolved in pyridine (2 mL), acetic anhydride (1 mL) was added and reaction mixture was stirred for 2 hours at room temperature. The solvent was distilled under vacuum and the residue was loaded onto silica gel (1 g) and purified by column chromatography (silica gel, eluent, hexane:diethyl-ether; 80:20) (134 mg, 84%); $^1$H NMR (300 MHz, CDCl$_3$) δ 7.14 (s, 2H, benzoyl Hs), 6.98 (d, 1H, =8.72 Hz), 6.85 (d, 1H, J=8.72 Hz), 3.93 (s, 3H, OMe), 3.86 (s, 3H, OMe), 3.80 (s, 6H, 2×OMe), 2.41 (s, 3H), 0.99 (s, 9H), 0.25 (s, 6H).

Step 5: 2-Bromo-7-acetoxy-3-(3,4,5-trimethoxybenzoyl)-6-methoxybenzofuran

To a stirred solution of 2-t-butyldimethylsilyl-7-acetoxy-3-(3,4,5-trimethoxybenzoyl)-6-methoxybenzofuran (120 mg, 0.44 mmol) in 1,2-dichloroethane (1 ml) at room temperature under nitrogen was added bromine (12 μl, 0.44 mmol) dropwise and the reaction mixture was stirred at this temperature for 10 minutes. After this time the reaction was quenched with saturated sodium thiosulfate solution, extracted with ethyl acetate (20 mL), dried over magnesium sulfate and the solvent removed by distillation under vacuum. The crude product was purified by silica gel column chromatography (eluent=Hexane:diethyl ether; 8:2-7:3) to afford the title compound as a colourless crystalline solid (91 mg, 81%); $^1$H NMR (300 MHz, CDCl$_3$) δ 7.40 (d, 1H, J=8.70 Hz), 7.14 (s, 2H, benzoyl-Hs), 6.98 (d, 1H, J=8.75 Hz), 3.94 (s, 3H, OMe), 3.89 (s, 3H, OMe), 3.86 (s, 6H, 2×OMe), 2.43 (s, 3H); $^{13}$C NMR (75 MHz, CDCl$_3$) δ 187.95 (CO), 167.71, 152.75, 149.54, 147.49, 142.59, 131.92, 131.80, 123.91, 121.84, 119.89, 117.72, 109.89, 106.92, 60.69, 56.61, 56.00, 20.09.

Example 1

Preparation of 2-Methyl-7-hydroxy-3-(3,4,5-trimethoxybenzoyl)-6-methoxybenzofuran

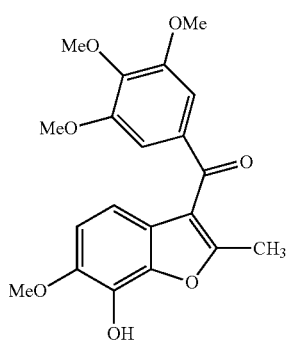 [SMILES: COc1cc(C(=O)c2c(C)oc3c(O)c(OC)ccc23)cc(OC)c1OC]

Preparation A

To a stirred solution of 2-Bromo-7-acetoxy-3-(3,4,5-trimethoxybenzoyl)-6-methoxybenzofuran (20 mg, 0.042 mmol), methyl-boronic acid (40 mg, 0.67 mmol), in 1,4-dioxane (2 mL) at 90° C. was added tetrakis-triphenylphosphine palladium (11 mg, 0.01 mmol) followed by the addition of a solution of sodium bicarbonate (40 mg, 0.48 mmol) in distilled water (0.5 mL). The reaction mixture turned red after 5 minutes. After 2 hours (tlc) the reaction mixture was brought to room temperature and was added saturated ammonium chloride mL) and diluted with dichloromethane (20 mL). The organic layer was separated and washed with water, dried over magnesium sulfate and the solvent was removed by distillation under vacuum. The residue was purified by PTLC (eluent=Dichloromethane/Methanol, 1:1) to give the title compound (acetate cleaved during reaction) as a fluffy white solid; (3 mg, 19%).

Preparation B (Negishi Coupling)

To a stirred solution of zinc-bromide (592 mg, 2.63 mmol) in dry THF (1.5 mL) at 0° C. was added the solution of methyl lithium (1.6 M solution in diethyl-ether, 2.6 mL, 4.15 mmol) and the reaction mixture was stirred for 2 hours. Solid 2-bromo-7-acetoxy-3-(3,4,5-trimethoxybenzoyl)-6-methoxy-benzofuran (300 mg, 0.63=1op was added and the ether was removed under vacuum and to the rest suspension was added dichlorobis(triphenylphosphine)palladium catalyst (21 mg) and catalytic amount of copper (I) iodide. The reaction mixture was stirred at room temperature for 36 hours (monitored by tlc), quenched with saturated ammonium chloride solution and extracted with dichloromethane (10 mL), dried over magnesium sulfate and solvent distilled under vacuum and the product was purified by silica gel column (eluent=hexane/ethyl acetate; 8:2). The product was crystallized in methanol (106 mg, 46%); $^1$H NMR (300 MHz, CDCl$_3$) δ 7.09 (s, 2H, benzoyl Hs), 6.93 (d, 1H, J=8.54 Hz), 6.83 (d, 1H, J=8.56 Hz), 5.70 (bs, 1H, OH), 3.93 (s, 3H, OMe), 3.92 (s, 3H, OMe), 3.83 (s, 6H, 2×OMe), 2.54 (s, 3H, 2-Me)

Example 2

Preparation of Disodium 6-methoxy-2-methyl-3-(3,4,5-trimethoxybenzoyl)benzofuran-7-yl phosphate

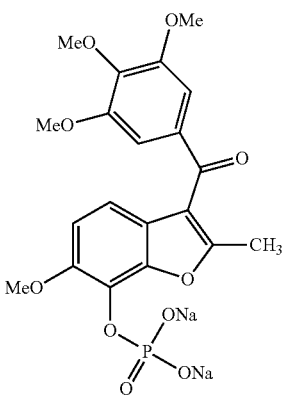

Step 1: Dibenzyl 6-methoxy-2-methyl-3-(3,4,5-trimethoxybenzoyl)benzofuran-7-yl phosphate To a mixture of 0.081 g (0.22 mmol) of (7-hydroxy-6-methoxy-2-methylbenzofuran-3-yl)(3,4,5-trimethoxyphenyl)methanone, 0.086 g (0.261 mmol) of carbon tetrabromide and 0.063 (0.283 mmol) of dibenzylphosphite in 2.5 ml of anhydrous acetonitrile 0.046 ml of anhydrous triethylamine was added dropwise at 0° C. under nitrogen atmosphere. The resulting mixture was stirred for 2 h at room temperature, then diluted to 20 ml with ethyl acetate, washed with water brine, dried over anhydrous magnesium sulfate, filtered off and evaporated to dryness under reduced pressure. The residue was purified by flash column chromatography (dichloromethane/ethyl acetate, 9:1) to give the title compound as a colorless foam (0.13 g, 94%); $^1$H NMR (CDCl$_3$) δ 2.42 (s, 3H, Me-2); 3.83 (s, OMe); 3.93 (s, 3H, OMe); 5.33 (m, 4H, CH$_2$Ph); 6.89 (d, CH aromatic, J=8.7 Hz); 7.21 (dd, CH aromatic, J=8.72 Hz; J=1.2 Hz); 7.08 (s, 2H, CH aromatic); 7.29-7.43 (m, 10H, CH aromatic).

Step 2: Disodium 6-methoxy-2-methyl-3-(3,4,5-trimethoxybenzoyl)benzofuran-7-yl phosphate To a stirred solution of 0.122 g (0.193 mmol) of the product from Step 1 in 1 ml of anhydrous acetonitrile 0.075 ml (0.58 mmol) of bromotrimethylsilane was added at −5° C. under nitrogen atmosphere. The resulting mixture was stirred for 1 h at 0° C. then evaporated to dryness 07 vacuo. The residue was diluted to 5 ml with anhydrous methanol and pH of the solution was brought tip about 10 by the addition of sodium methoxide. After evaporation of the resulting mixture under reduced pressure the solid residue was washed with anhydrous isopropanol (4×1.5 ml) and anhydrous ethanol (3×1.5 ml) and dried under vacuum to give 0.062 g (65% yield) of title compound as an colorless solid; $^1$H NMR (D$_2$O) δ 2.37 (s, 3H, Me-2); 3.76 (s, 6H, OMe); 3.79 (s, 3H, OMe); 3.82 (s, 3H, OMe); 4.66 (s, H$_2$O); 6.93 (d, 1H, CH aromatic, 0.1-8.6 Hz); 7.04 (d, 1H, CH aromatic, J=8.6 Hz); 7.10 (s, 2H, CH aromatic).

Biological Data
Materials and Methods
Reagents

Example 2 (EX2) used in these studies was obtained from Bionomics Ltd. ABT-199 was purchased from Active Biochem. Dinaciclib was obtained from the Cancer Therapy Evaluation Program, National Cancer Institute, c-Jun-NH2-terminal kinase (JNK) inhibitor VIII was purchased from Calbiochem. Hoechst 33342 was purchased from Molecular Probes. Vinblastine, combretastatin A and other reagents were purchased from Sigma.

The following antibodies were used: phospho-c-Jun (Ser-63; 9261), phospho-JNK1/2 (9255), JNK1/2 (9252), and poly ADP ribose polymerase (PARP; 9542; Cell Signaling); Noxa (OP180) and actin (EMD Biosciences; JLA20). Secondary antibodies were purchased from BioPRad.

Cell Culture

CLL cells were obtained from consented patients at the Norris Cotton Cancer Center. Cells were purified by centrifugation in Ficoll-Paque PLUS from 10 ml, of blood. Lymphocytes were plated in RPMI 1640 plus 10% serum at 1×10$^6$ cells/mL after three washes in PBS+2 mmol/L EDTA. Cells were either incubated immediately with reagents or after 24 h incubation with confluent layers of CD154+ stromal cells (L 4.5) at a ratio of 5:1.

Chromatin Staining

Cells were incubated for 10 min with 2 μg/mL Hoechst 33342 at 37° C. and visualized with a fluorescent microscope. At least 200 cells were scored for each sample. The percentage of cells with condensed chromatin was recorded.

Immunoblot Analysis

Cells were lysed in urea sample buffer [4 mol/L urea, 10% β-mercaptoethanol, 6% SDS, 125 Tris (pH 6.8), 0.01% bromphenol blue, and protease/phosphatase inhibitor cocktail] and boiled for 5 min. Proteins were subsequently separated by SDS-PAGE (10 or 15%) and transferred to polyvinylidene difluoride membrane (Millipore). Membranes were blocked with 5% nonfat milk in TBS and 0.05% Tween 20, and were probed with the appropriate primary antibody overnight. Subsequently, membranes were washed in MS and 0.05% Tween 20, and then incubated with secondary antibody conjugated to horseradish peroxidase. Proteins were visualized by enhanced chemiluminescence (Amersham). Actin was used as a loading control in Western blots.

Results
Single Agent Efficacy of EX2 in CLL Cells

Figure 1B:
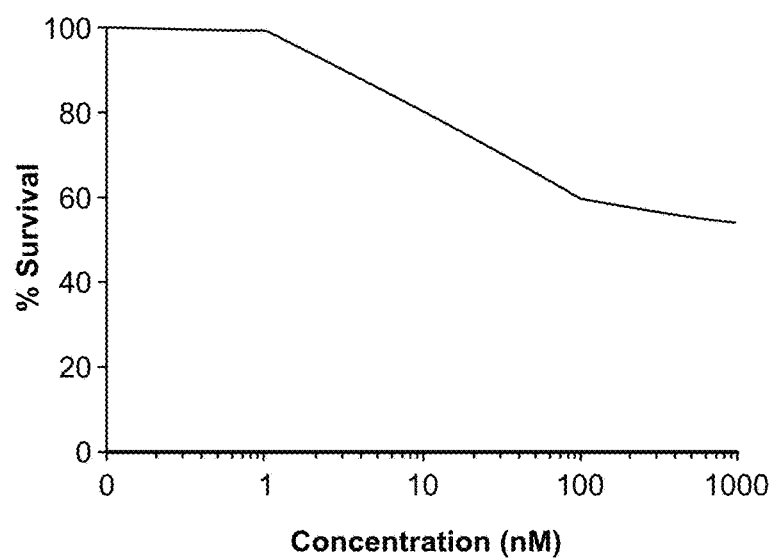

To determine whether EX2 induces apoptosis, freshly isolated CLL cells were incubated in media containing 0-1 μM EX2. Chromatin condensation was scored as a classic marker of apoptosis. Apoptosis was observed following incubation of cells with 10-100 nM EX2 and this also correlated with the cleavage of PARP (FIG. 1). Protein lysates were also assessed for both pJNK and NOXA, both of which were increased by the same concentrations of EX2.

Figure 2A:
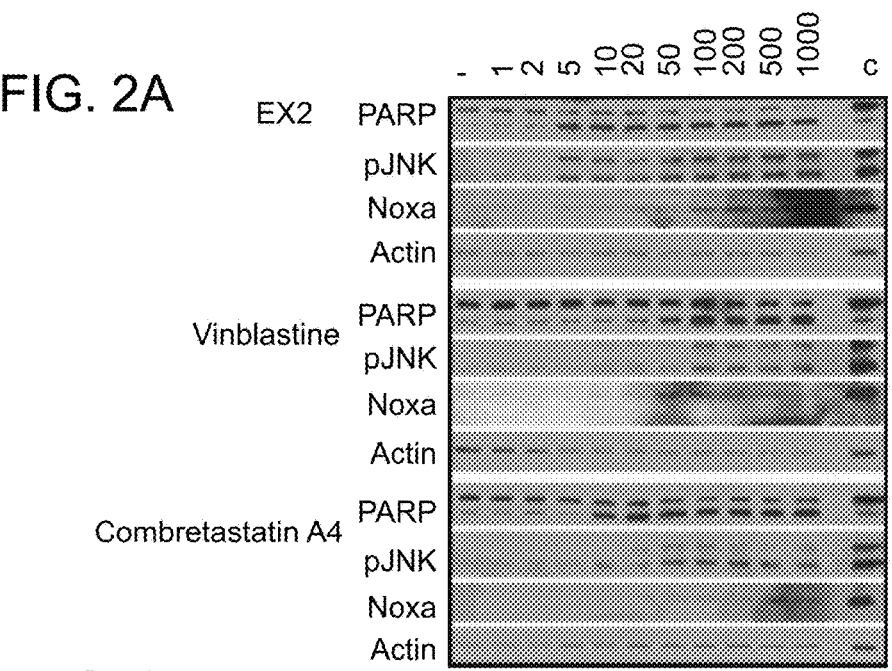
FIG. 2A, 2B and 2C depict that compounds of formula (I) are the more potent apoptosis inducers in CLL cells.
Figure 2B:
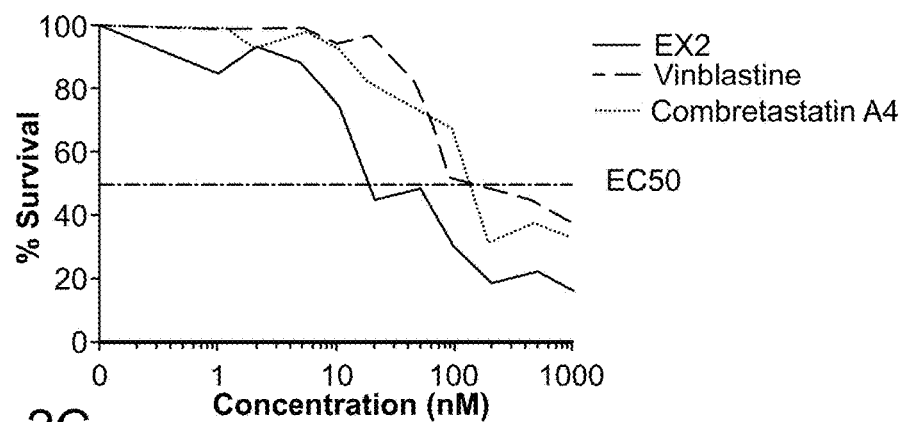
Figure 2C:
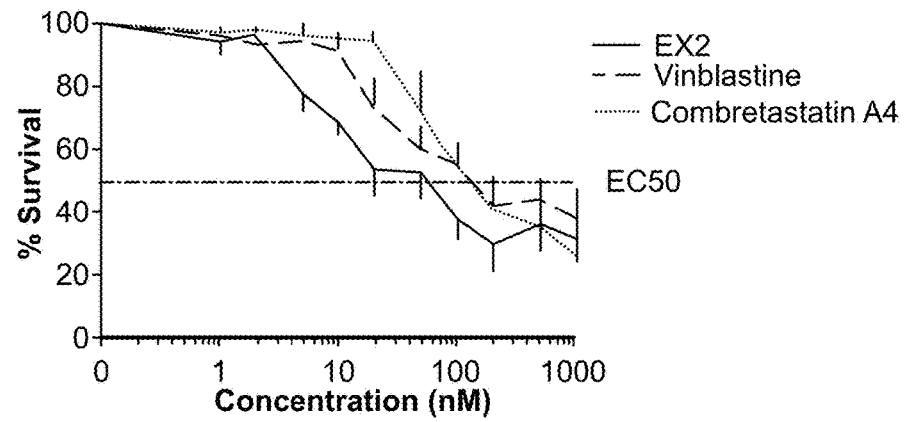
Figure 3A:
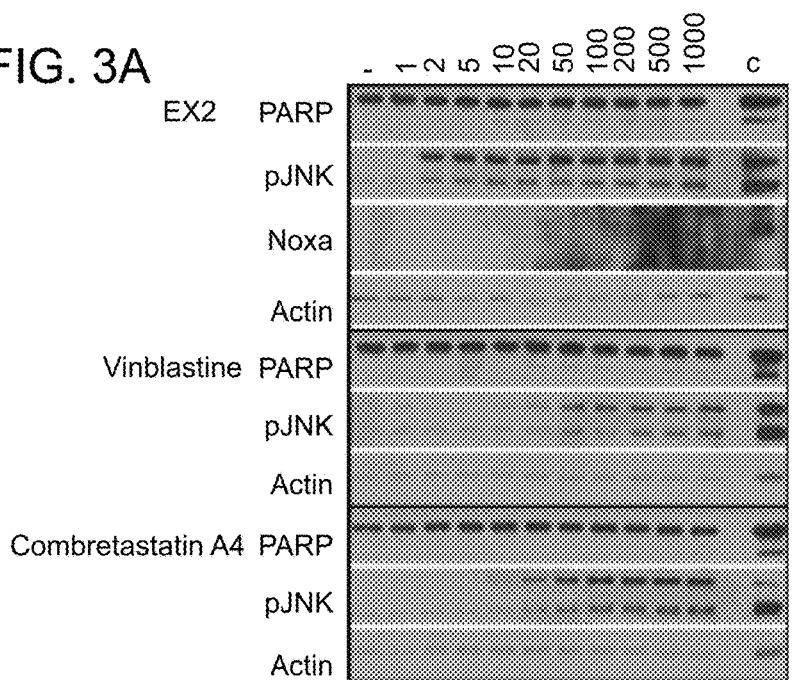
FIG. 3A and 3B depict that CLL cells are resistant to three microtubule targeting drugs.
Figure 3B:
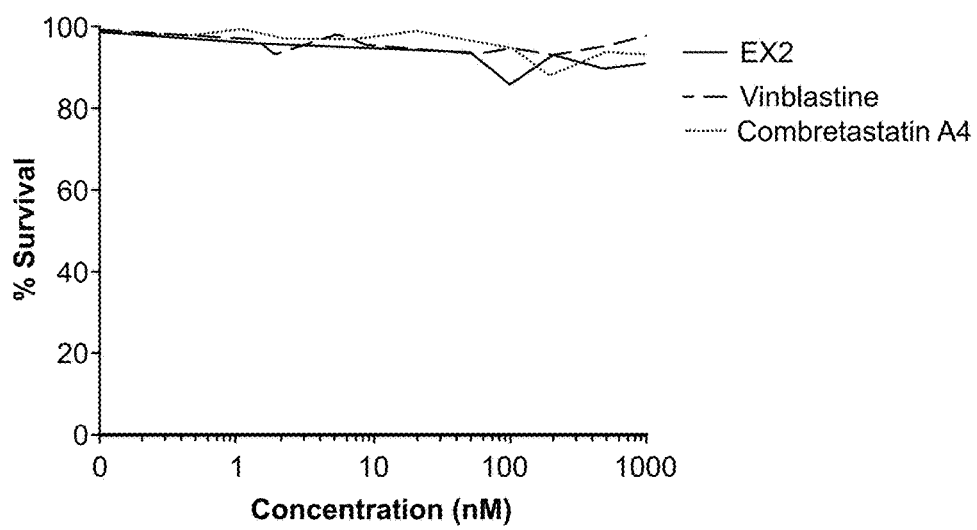

We next compared the efficacy of three microtubule disrupting agents, EX2, vinblastine and combretastatin A4, in greater detail. FIGS. 2A and B reflect one individual patient, while FIG. 2C reflects an average of 3-6 patients. EX2 is the more potent inducer of apoptosis in CLL cells, as assessed by both chromatin condensation and PARP cleavage. In each case, pJNK and Noxa expression correlated with the appearance of apoptosis, which in the case of EX2 began to appear at concentrations as low as 5 nM (FIG. 2A).

Apoptosis Induced in CLL Cells is JNK Dependent

Figure 4A:
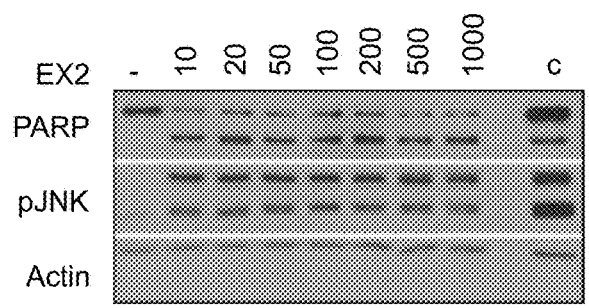
FIG. 4A, 4B and 4C depict that compounds of formula (I)-induced apoptosis in CLL cells is JNK dependent.
Figure 4B:
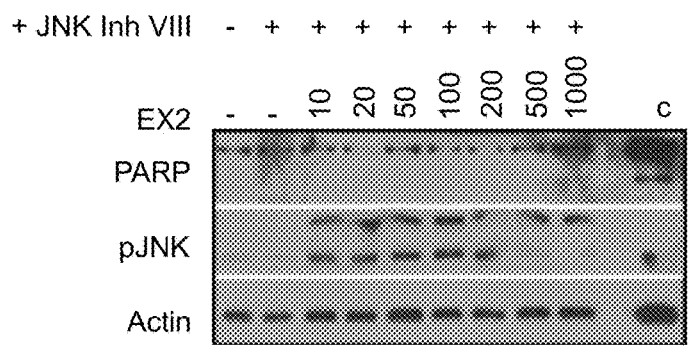
Figure 4C:
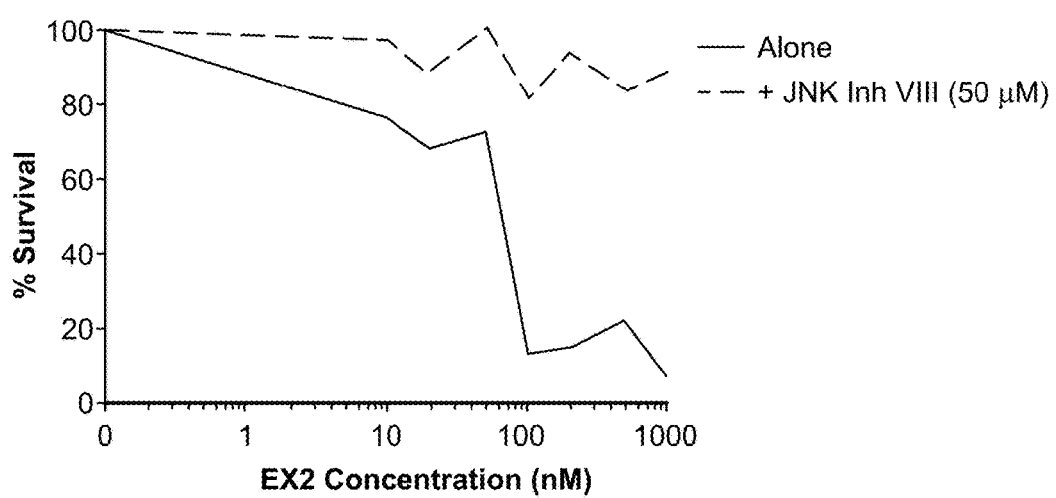
Figure 5A:
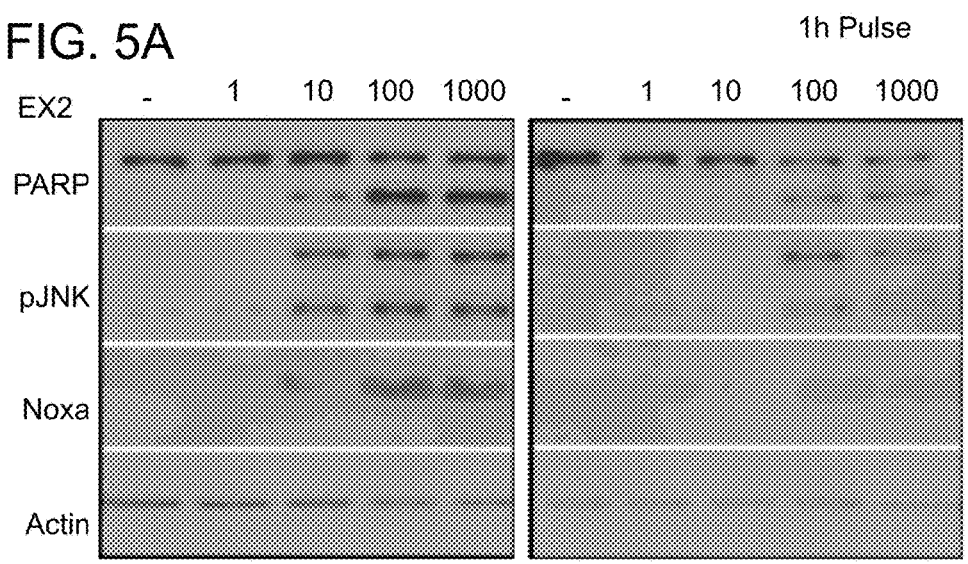
FIG. 5A and 5B depict that compounds of formula (I) induce apoptosis after 1-h pulse incubation in CLL cells.
Figure 5B:
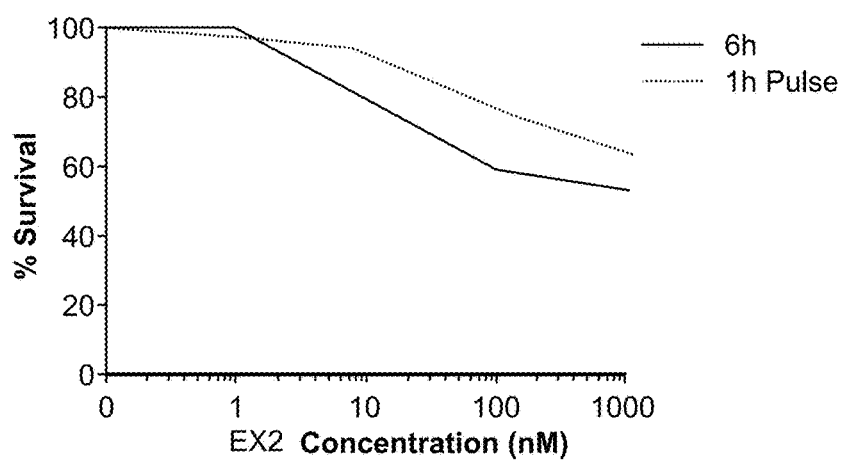

CLL cells were incubated with 0-1 μM EX2 in the presence or absence of the JNK inhibitor VIII. PARP cleavage is seen in the absence of the inhibitor but is completely prevented by the JNK inhibitor (FIGS. 4A, B, and 11A, B), and this correlates with the observed cell survival measured by condensed chromatin staining (FIG. 4C).

Phosphorylated JNK is observed in all conditions with and without the inhibitor. These results suggest that the mechanism leading to apoptosis induced by EX2 in CLL cells is dependent on pJNK activity.

The activation of JNK occurs rapidly (in less than one hour). It was then determined whether a 1 h pulse treatment with EX2 would be as effective as a continuous incubation with EX2. Five hours after removing EX2, JNK activation and PARP cleavage were still observed albeit slightly less than when the EX2 was incubate with the cells continuously.

Figure 6:
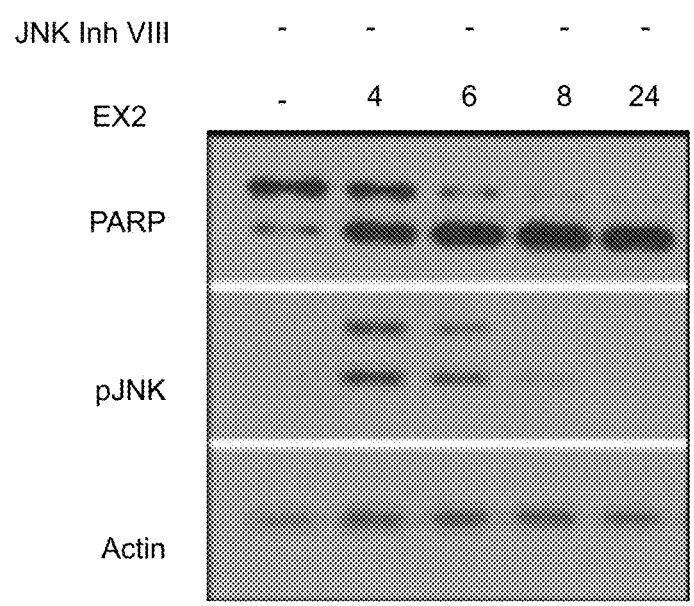
FIG. 6 depicts the kinetics of compounds of formula (I)-induced apoptosis in CLL cells. Western blots of CLL cells from patient 114 were incubated with 20 μM compounds of formula (I).
Figure 7:
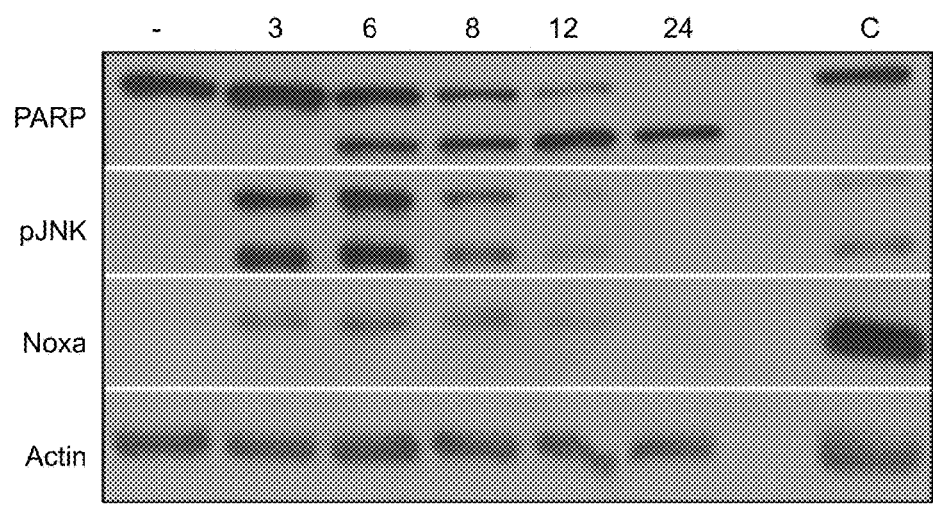
FIG. 7 depicts the kinetics of compounds of formula (I)-induced apoptosis in Jeko-1 cells. Western blots of Jeko-1 cells were incubated with 20 μM compounds of formula (I). "C"=a control cell line incubated with 2 μM vinblastine as a positive control for protein expression.

It was noted that in many of these experiments, PARP cleavage was incomplete at 6 h. To determine whether greater apoptosis occurred at later time points, we incubated cells for up to 24 h with EX2 (FIG. 6). Apoptosis increased over this time frame with almost total cleavage of PARP observed by 24 h, albeit the example shown appears to be particularly sensitive to EX2 even at 6 h. However, in a parallel experiment using Jeko-1 cells, it was found that the majority of apoptosis occurred between 6 and 12 h and was complete by 24 h (FIG. 7). Hence it appears that apoptosis is not restricted to any subpopulation but can occur in the entire population of cells.

Figure 12A:
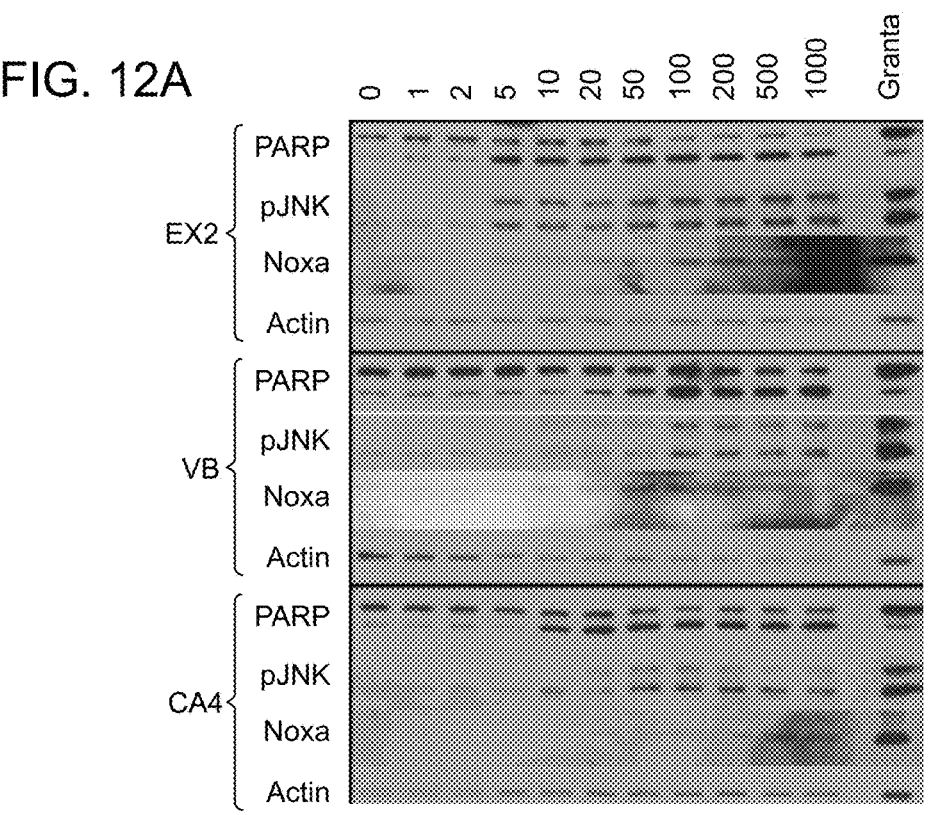
FIG. 12A and 12B depict that compounds of formula (I) are more potent than vinblastine or CA4 at activating JNK, inducing Noxa and apoptosis in CLL cells ex vivo. Freshly isolated CLL cells were incubated with EX2, vinblastine or CA4 for 6h ex vivo and then analysed.
Figure 12B:
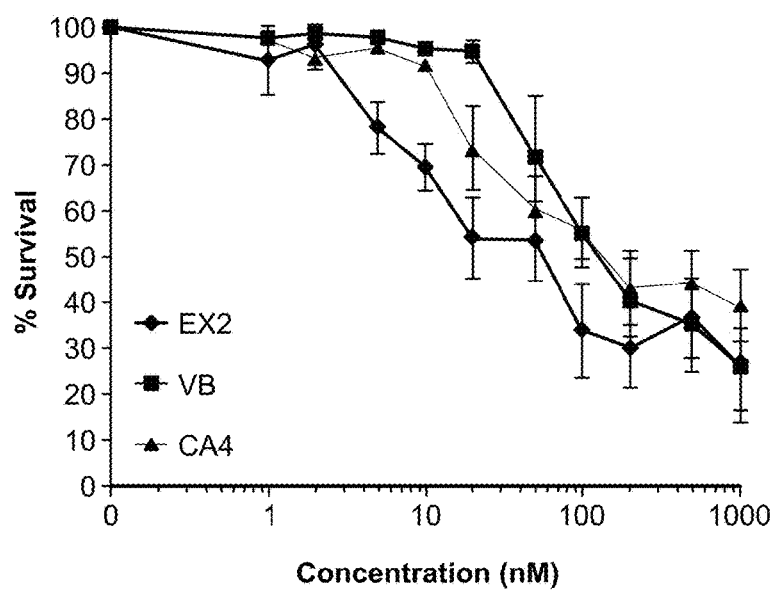

In FIG. 12 freshly isolated CLL cells were incubated with EX2, vinblastine or CA4 for 6 h ex vivo, and then analyzed for (A) protein expression (representative example shown) and (b) apoptosis (n=4).

Figure 8A:
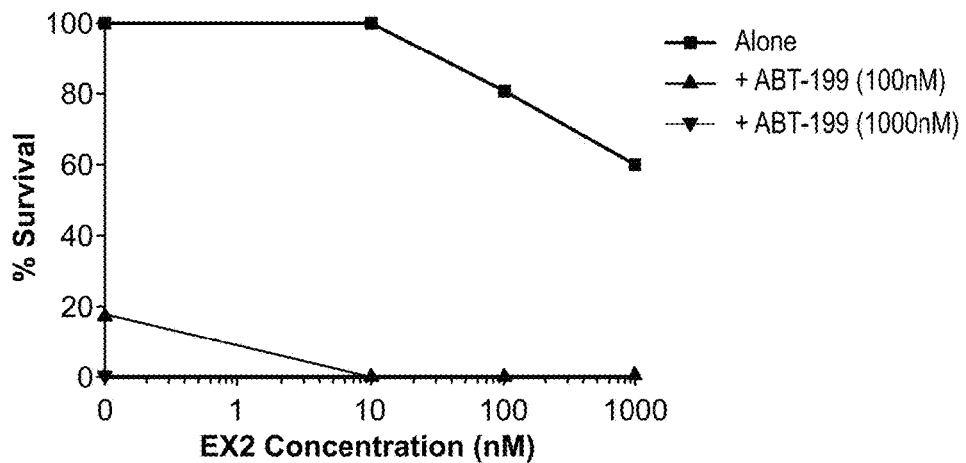
FIGS. 8A, 8B and 8C depict that compounds of formula (I) sensitize peripheral CLL cells to ABT-199 incubated on stroma.
Figure 8B:
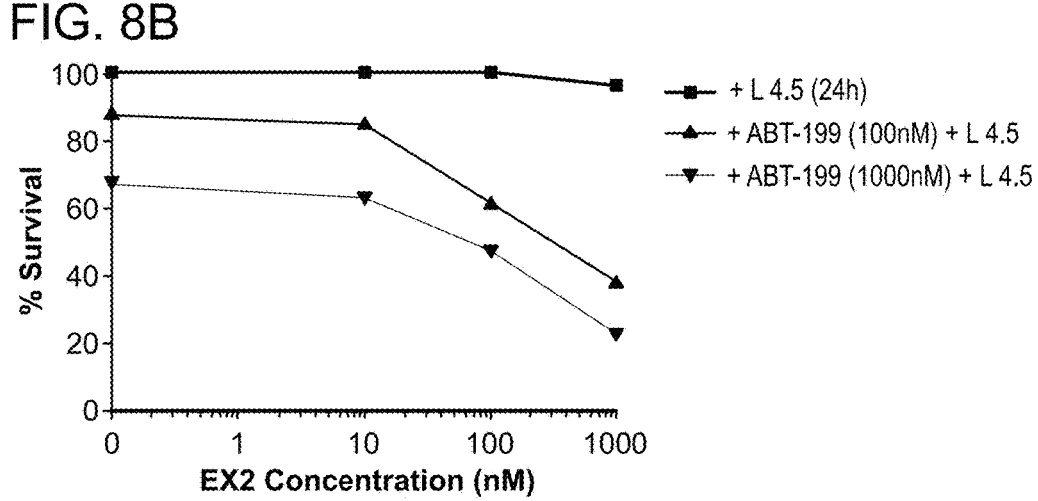
Figure 8C:
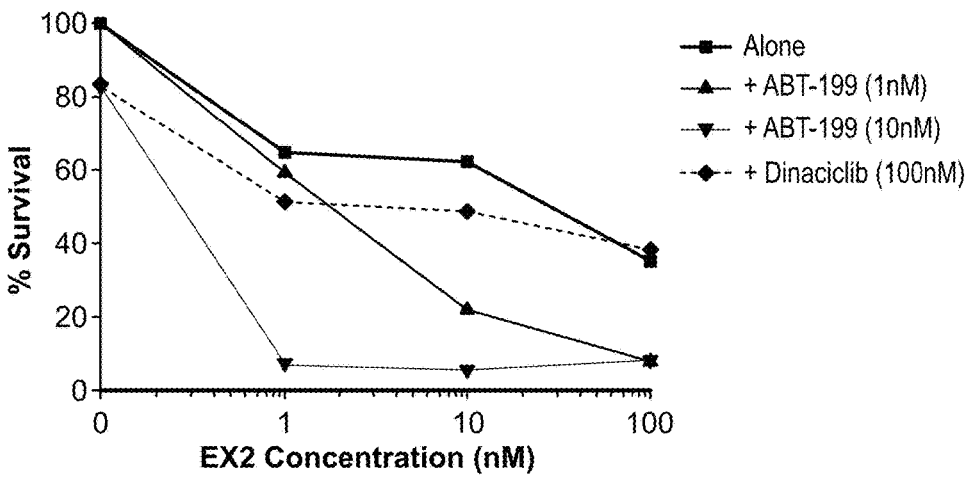

Stroma Mediates Resistance to EX2 which can be Circumvented by Novel Drug Combinations The experiments above have shown that CLL cells are usually very sensitive to EX2. However, these cells were isolated from peripheral blood, and the real problem to curing CLL is to be able to kill cells that reside in the lymph node or hone marrow niche. To mimic this niche, we have used L4.5 cells that express CD154. Co-incubation of CLL cells on this stroma for 24 h elicits marked resistance to many drugs including the BCL-2 inhibitor ABT-199 (FIG. 8). These co-cultured CLL cells are also markedly resistant to EX2 with no apoptosis observed at 1 μM (FIG. 8). However, when ABT-199 and EX2 were combined, marked apoptosis was again observed. For example, 100 nM ABT-199 alone induced about 10% apoptosis, whereas when combined with 1 μM EX2, >60% apoptosis was observed within 6 h. The combination of 1 μM EX2 and 1 μM ABT-199 induced about 80% apoptosis. This patient's cells appeared to be more resistant than those summarized in FIG. 2 which may therefore understate the impact of this combination. In cells from another patient that were more sensitive to EX2 alone we observed greater sensitization to ABT-199; these cells were not tested on stroma.

Normal Peripheral Lymphocytes are Resistant to EX2

Figure 9A:
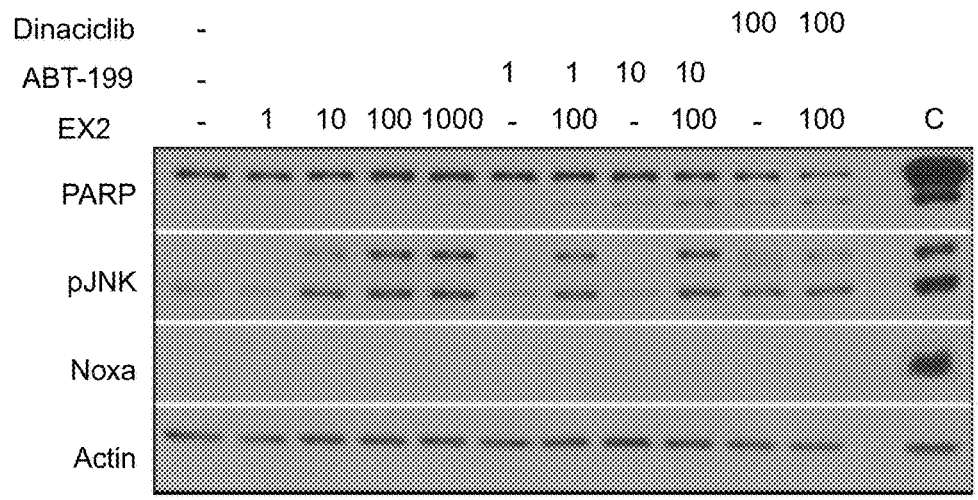
FIGS. 9A and 9B depict that compounds of formula (I) show no toxicity to normal peripheral lymphocytes and does not sensitize the cells to ABT-199.
Figure 9B:
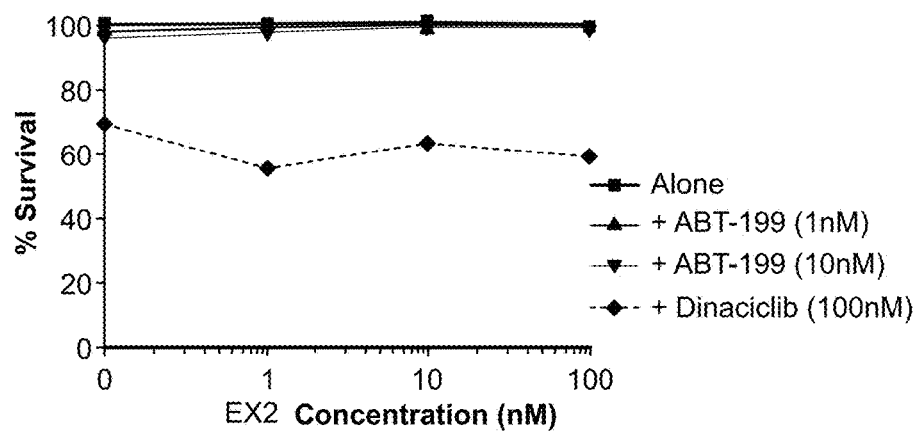
Figure 10:
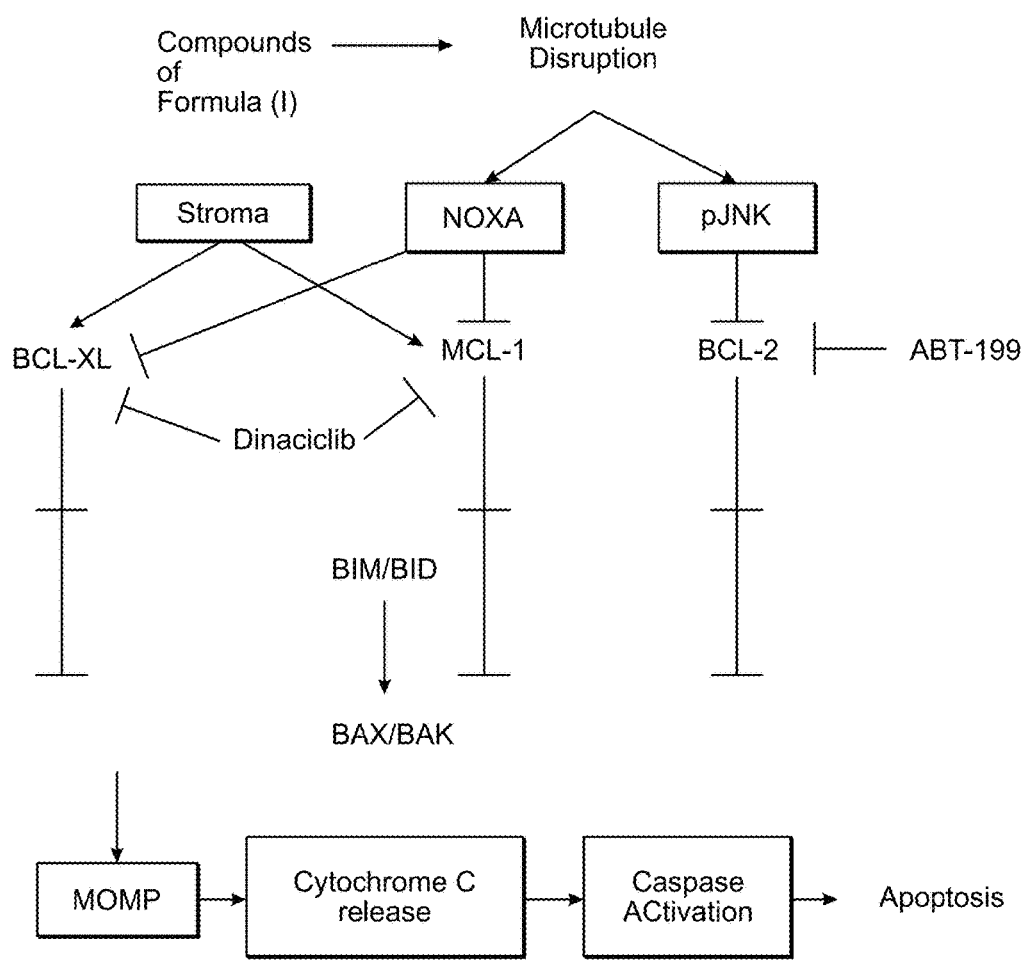
FIG. 10 depicts possible mechanism of action of Compounds of formula (I) leading to apoptosis. Compounds of formula (I) bind to the colchicine site in microtubules, disrupting dynamic stability and resulting in tubulin depolymerization. As result, JNK is phosphorylated and Noxa is induced. pJNK can activate a phosphorylation cascade causing inhibition of BCL-2. Noxa binds to MCL-1 targeting it for degradation. Transcription inhibition by the CDK inhibitor dinaciclib results in a rapid decrease in levels of MCL-1. Pro=-apoptotic activators (e.g., BIM, BID) and effectors (e.g., BAX, BAK) interact leading to apoptosis. Co-culture with stromal cells causes protection through upregulation of BCL-XL and MCL-1 (and potentially BFL1, not shown). The BH3 mimetic ABT-199 inhibits only BCL-2 and will kill peripheral CLL cells, but not those on stroma. Any agent that induces Noxa (compounds of formula (I)) or inhibits MCL1/BCL-X expression (dinaciclib) can sensitize cells to ABT-199.
Figure 11A:
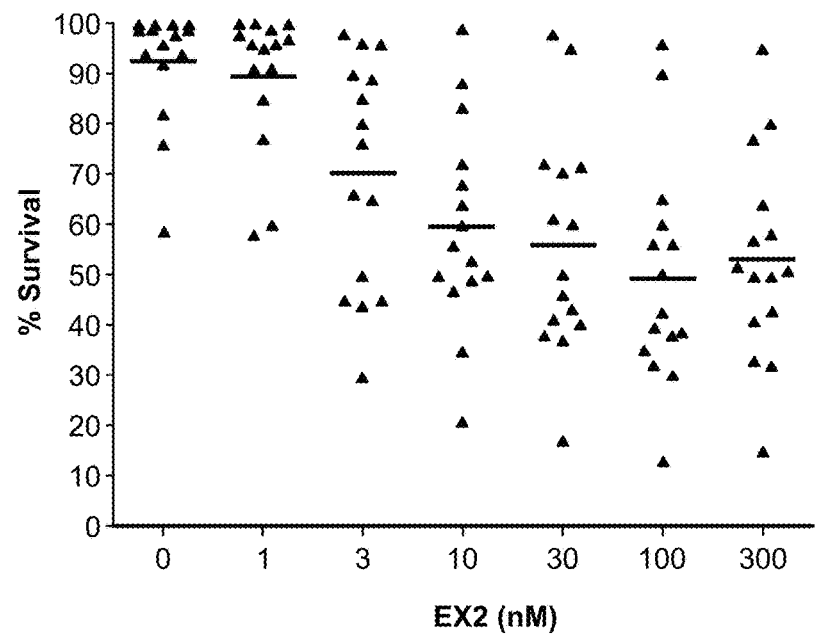
FIG. 11A and 11B depict that compounds of formula (I) induce JNK-dependant apoptosis in CLL cells ex vivo.
Figure 11B:
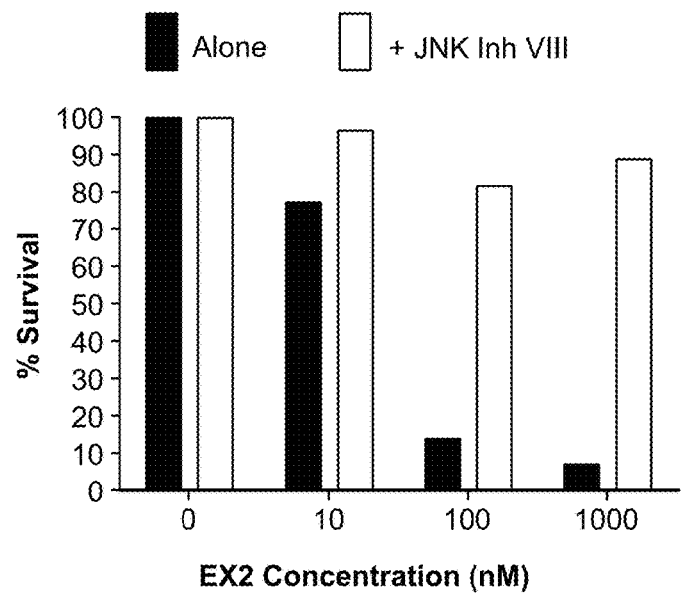

To test the potential toxicity of EX2, normal peripheral lymphocytes were isolated from a healthy volunteer and incubated with EX2 alone or in combination with ABT-199. There was no significant PARP cleavage or chromatin condensation induced by EX2, although pJNK was activated; however, no Noxa was induced (FIG. 9), ABT-199 appeared to induce slight PARP cleavage but this was not increased by EX2, and no chromatin condensation was observed. This figure also shows the impact of combining EX2 with the CDK9 inhibitor dinaciclib, which functions in this model primarily by preventing expression of MCL-1. Dinaciclib alone induced some apoptosis in normal leukocytes but this was not increased by EX2.

Figure 13A:
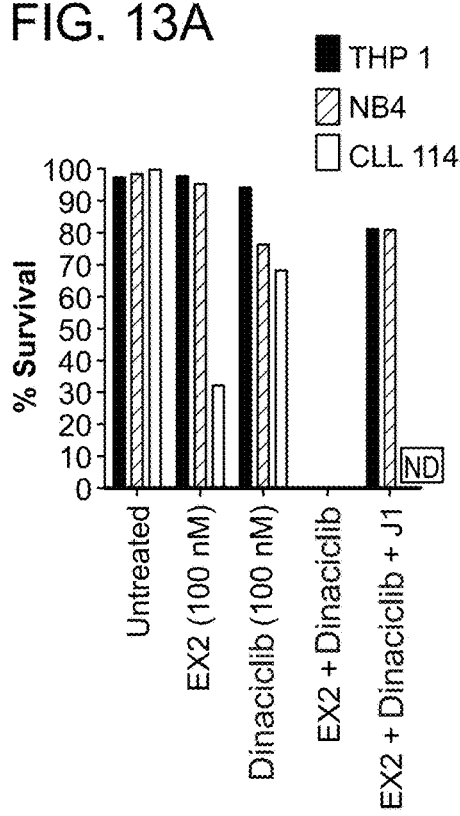
FIGS. 13A, 13B and 13C depict that compounds of formula (I) enhance apoptosis induced by ABT-199 or dinaciclib.
Figure 13B:
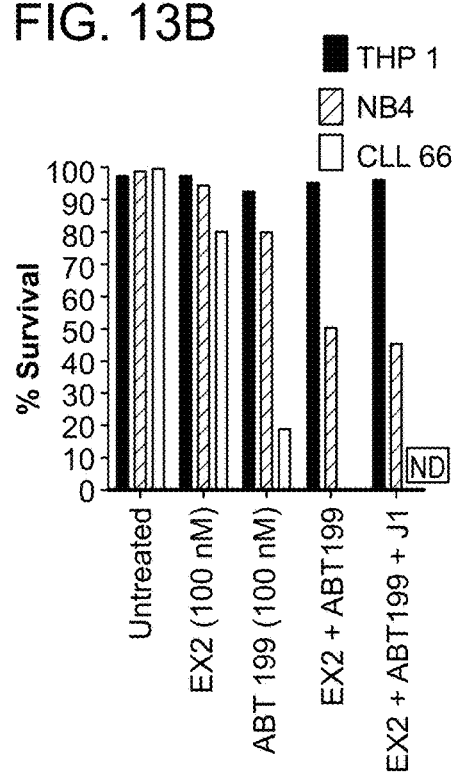
Figure 13C:
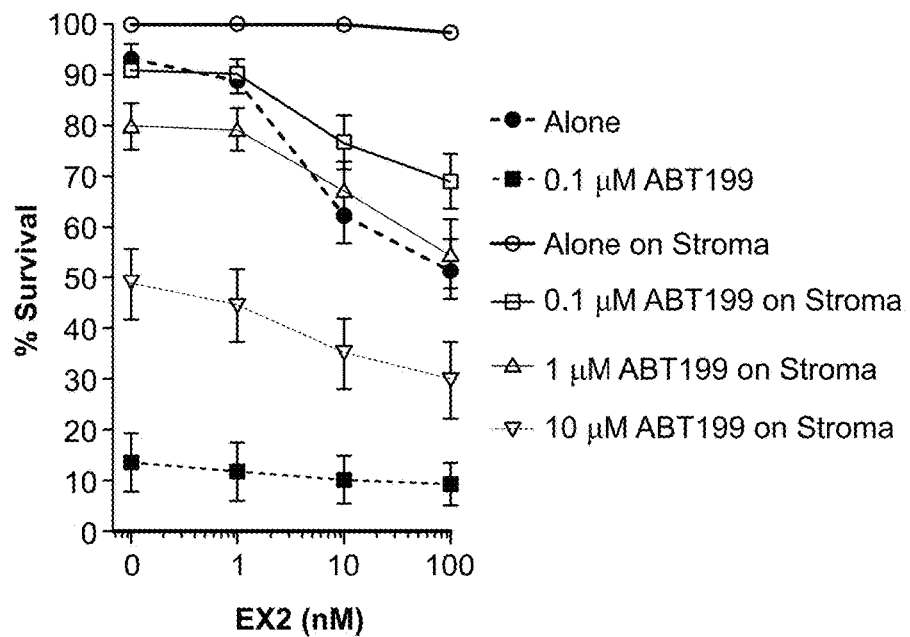

FIG. 13 shows Leukemia cell lines of CLL cells were incubated with EX2±dinaciclib (A) or ABT-199 (B) for 6 h. Consistent with previous vinblastine results, dinaciclib-mediated apoptosis requires JNK but ABT-199-mediated apoptosis does not, (C) Freshly isolated CLL cells were incubated alone and treated immediately, or plated on top of a monolayer of CD40L expressing L4.5 stroma cells for 24 h, then treated for 6 h with EX2±ABT-199 (n=16).

The claims defining the invention are as follows:

1. A method for treating chronic lymphocytic leukemia (CLL) in a patient, the method comprising administering to the patient an effective amount of a compound of formula (I) or a salt, solvate or prodrug thereof

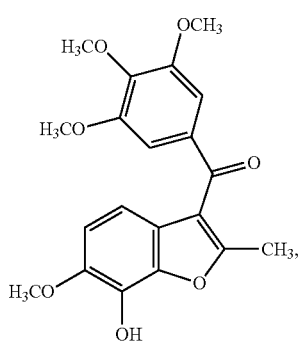

thereby treating CLL in the patient.

2. The method of claim 1 wherein the patient is a human subject.

3. The method of claim 1 wherein the effective amount administered is from about 0.05 to 20 mg/kg body weight per day.

4. The method of claim 1 wherein the effective amount administered is from about 0.4 mg to 16 mg/kg body weight per day.

5. The method of claim 1 wherein the compound is administered by oral or parenteral administration.

6. The method of claim 1 wherein the compound is co-administered simultaneously or sequentially with another anti-cancer agent.

7. The method of claim 1 wherein the patient is selected for treatment based on clinical parameters including age, level of progression of the disease, and/or other complicating ailments.

8. The method of claim 1, wherein the compound of formula (I) is:

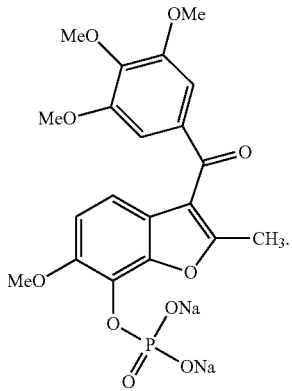

* * * * *